United States Patent
Chesavage et al.

(10) Patent No.: US 12,274,451 B2
(45) Date of Patent: Apr. 15, 2025

(54) BLUETOOTH COMMUNICATION PROTOCOL FOR A PRESSURE CONTROLLER

(71) Applicant: VASPER SYSTEMS LLC, Kamuela, HI (US)

(72) Inventors: Jay A. Chesavage, Palo Alto, CA (US); Marshall Lise, Mountain View, CA (US); Eric Hoffman, San Francisco, CA (US)

(73) Assignee: Vasper Systems, LLC, Kamuela, HI (US)

( * ) Notice: Subject to any disclaimer, the term of this patent is extended or adjusted under 35 U.S.C. 154(b) by 588 days.

(21) Appl. No.: 17/225,059

(22) Filed: Apr. 7, 2021

(65) Prior Publication Data

US 2021/0219988 A1    Jul. 22, 2021

Related U.S. Application Data

(63) Continuation of application No. 15/085,859, filed on Mar. 30, 2016, now Pat. No. 10,993,727.

(51) Int. Cl.
| | |
|---|---|
| *A61B 17/135* | (2006.01) |
| *A61H 9/00* | (2006.01) |
| *F04B 23/02* | (2006.01) |
| *F04B 49/06* | (2006.01) |
| *F04B 49/20* | (2006.01) |

(52) U.S. Cl.
CPC ........ *A61B 17/1355* (2013.01); *A61B 17/135* (2013.01); *A61H 9/00* (2013.01); *A61H 9/0078* (2013.01); *A61H 9/0092* (2013.01); *F04B 23/02* (2013.01); *F04B 49/065* (2013.01); *F04B 49/20* (2013.01); *A61H 2201/02* (2013.01); *A61H 2201/0242* (2013.01); *F04B 2205/06* (2013.01)

(58) Field of Classification Search
CPC .................................................. A61B 17/1355
See application file for complete search history.

(56) References Cited

U.S. PATENT DOCUMENTS

| | | | |
|---|---|---|---|
| 10,201,503 B1 * | 2/2019 | Li | B29C 64/295 |
| 2007/0224712 A1 * | 9/2007 | Kaushal | H01L 21/67253 |
| | | | 438/15 |
| 2011/0227711 A1 * | 9/2011 | Weimer | H04Q 9/00 |
| | | | 340/12.5 |

\* cited by examiner

*Primary Examiner* — Hsinchun Liao
(74) *Attorney, Agent, or Firm* — File-EE-Patents.com; Jay A. Chesavage

(57) ABSTRACT

A pressure controller for a fluidic bladder has in sequence a pump, a first fluid line, a supply pressure sensor, a second fluid line, a bladder having an inlet coupled to the second fluid line, a bladder outlet coupled to a third fluid line of substantially equal length to the second fluid line, a return pressure sensor, and a fourth fluid line coupled to the return pressure sensor and returning fluid from the pump to the reservoir. A pressure estimate is formed by establishing the second fluid line length and inner diameter as the same as the third fluid line length and inner diameter, and forming the pressure estimate by averaging the supply pressure and return pressure. The pressure controller receives a setpoint pressure as a command and data over a wireless channel, and computes a head pressure offset by turning the pump off and measuring the supply and return pressures.

9 Claims, 11 Drawing Sheets

Four Cuff Arm/Leg Pressure/Cooling System 600

*Figure 1*
Pressure Control System

*Figure 2*
Flow Schematic

*Figure 3*
Pressure Control System

Figure 4

*Figure 6*
Four Cuff Arm/Leg Pressure/Cooling System
600

Figure 7

Figure 8
Unscrambled Data

Unscrambled Command Byte

| 7 | 6 | 5 | 4 | 3 | 2 | 1 | 0 |
|---|---|---|---|---|---|---|---|
| 0 | 0 | c5 | c4 | c3 | c2 | c1 | c0 |

Unscrambled Data Byte

| 7 | 6 | 5 | 4 | 3 | 2 | 1 | 0 |
|---|---|---|---|---|---|---|---|
| d7 | d6 | d5 | d4 | d3 | d2 | d1 | d0 |

Figure 9
Scrambled Data

Scrambled Command Byte

| 7 | 6 | 5 | 4 | 3 | 2 | 1 | 0 |
|---|---|---|---|---|---|---|---|
| 1 | d7 | c5 | c4 | c3 | c2 | c1 | c0 |

Scrambled Data Byte

| 7 | 6 | 5 | 4 | 3 | 2 | 1 | 0 |
|---|---|---|---|---|---|---|---|
| 0 | d6 | d5 | d4 | d3 | d2 | d1 | d0 |

*Figure 10*
Controller Process

Figure 12
Controller

Figure 13
Pressure Regulator State Machine

BLUETOOTH COMMUNICATION PROTOCOL FOR A PRESSURE CONTROLLER

FIELD OF THE INVENTION

The present invention relates to a system and method for measurement or regulation of pressure inside a bladder. In particular, the system relates to the measurement and regulation of pressure in a bladder having an input line and an output line and pressurized to a setpoint using a circulating fluid, and with an elevation difference between a remote measurement point and a bladder having an internal bladder setpoint pressure to measure or regulate.

BACKGROUND OF THE INVENTION

Measurement of fluidic pressure in a fluid-carrying bladder can be readily performed at the bladder using a pressure gauge or pressure sensor. However, when there is a circulating fluid through the bladder and the pressure sensor is remotely located from the bladder, several errors are introduced. A first error is an offset error associated with the fluid density and elevation difference between the bladder and pressure sensor. When the objective of the bladder is compression of a wearable cuff, the fluid used to pressurize the bladder can be air, in which case the added pressure from the elevation difference between bladder and sensor is a negligible 0.0323 Pascals (Pa) per mm. However, when the objective of the bladder is compression and also cooling of an encircled limb, water or other fluid with greater density and greater thermal transfer characteristics may be used. Where fluid is used as a coolant, the added fluid pressure from the vertical (elevation) difference between the bladder and pressure sensor measurement point, known as "head pressure", increases at the rate of 9.8 Pa per mm of vertical separation, or head height. In an example where the bladder pressure is 50 mmHg (6.67 kPa), and the pressure sensor is 750 mm below the bladder, the head pressure from the water in the lines from the bladder to the pressure sensor is 7.3 kPa, in excess of the intrinsic 6.67 kPa pressure to be measured. Further, when it is desired to measure the fluid pressure in the presence of fluid flow, the problem becomes yet more complicated by the pressure drops across the lines from turbulent flow in the fluid supply and return lines.

It is additionally desired to provide a reliable method for wireless control of pressurized fluid which travels through a bladder such that the pressure control may be performed locally to the cooling device and pressure commands can be issued over a wireless interface without risk of loss of pressure control or loss of regulation.

It is desired to provide a method and apparatus for measurement of fluidic pressure where a fluid is circulating through a bladder with a height difference between the bladder and the pressure sensor.

Objects of the Invention

A first object of the invention is a measurement system for estimation of the pressure of a fluid circulating through a bladder, the system having, in sequence, a variable speed motor coupled to a pump which is fluidly coupled to a reservoir, a first fluid line coupled to a supply pressure sensor, a second fluid line coupled to a bladder inlet port, a bladder outlet port coupled to a third fluid line of substantially equal flow parameters as the second fluid line, such as equal inner diameter and length as the second fluid line, the outlet of the third fluid line coupled to a return pressure sensor, the return pressure sensor coupled to a fourth fluid line returning circulated fluid to the reservoir, the bladder internal pressure estimated by taking the average of the supply pressure sensor measurement and return pressure sensor measurement.

A second object of the invention is a pressure control system for regulation of a pressure developed in a bladder to a setpoint, the pressure control system having:
  a reservoir fluidly coupled to the inlet of a variable speed pump, the variable speed pump having a fluid outlet coupled to, in sequence, a supply pressure sensor, a first fluid line coupled to an inlet port of a bladder, the bladder having an outlet port coupled to the inlet port, the bladder outlet port having a second fluid line coupled to a return pressure sensor, the return pressure sensor having an outlet which is either coupled to a reservoir or to a third fluid line coupled to the reservoir;
  the variable speed pump electrically controlled by a control system which generates a pump control signal which is coupled to the variable speed pump, the pump control signal being the linear combination of a first term derived from the difference between the setpoint and average pressure, and a second term derived from an integration of the difference between the setpoint and average pressure, the average pressure being the average of the supply pressure sensor measurement and the return pressure sensor measurement.

A third object of the invention is a pressure control system for regulation of a pressure developed in a bladder to a pressure setpoint, the pressure control system having:
  a reservoir fluidly coupled to a variable speed pump, the variable speed pump fluidly coupled to, in sequence, a supply pressure sensor, a first fluid line coupled to an inlet port of a bladder, the bladder having an outlet port coupled to the inlet port, the bladder outlet port having a second fluid line coupled to a return pressure sensor, the return pressure sensor having an outlet which is either coupled to a reservoir or to a third fluid line coupled to the reservoir;
  the variable speed pump controlled by a control system which generates a pump control signal which is electrically coupled to the variable speed pump, the pump control signal being the sum of a first term and a second term, where:
  the first term is formed from the product of a first constant multiplied by the difference between the setpoint and the average of the supply pressure and return pressure;
  and the second term is formed from the product of a second constant multiplied by the integral of the difference between the setpoint and the average of the supply pressure and return pressure over time.

A fourth object of the invention is the estimation and compensation of head pressure in a pressure regulation system receiving a setpoint pressure and generating a pressure to a remote bladder, the pressure regulation system having, in sequence, a reservoir fluidly coupled to the variable speed pump, a first fluid line, a supply pressure sensor, a second fluid line, a bladder inlet, a bladder outlet, a third fluid line, a return pressure sensor, and fourth fluid line coupled to the reservoir, the variable speed pump operated for a duration sufficient to develop a return pressure indicating the system is charged with coolant, the head pressure estimate formed by turning off the pump and measuring a return pressure and a supply pressure as back pressure from the fluid draining from the bladder, deriving a head pressure measurement from the return pressure measurement and supply pressure measurement, thereafter regulating to the pressure setpoint plus head pressure estimate, where the head pressure estimate may optionally be an manually assigned value until a head pressure estimate is measured.

SUMMARY OF THE INVENTION

The present invention is a pressure measurement and control system for a fluidic bladder developing a pressure using circulating fluid coupled, in sequence, from a reservoir and variable speed pump to a supply pressure sensor located near to the reservoir, to a length of supply fluid line, to the fluidic bladder, to a length of return fluid line, to a return pressure sensor located near the reservoir, and to the reservoir. The fluid lines are typically flexible hoses which are of a narrower inner diameter to restrict flow compared to any flow restriction into or out of the bladder to which they are coupled. In one example of the invention, a variable speed pump draws a coolant such as chilled water from a reservoir, pressurizes the coolant, and delivers the coolant, in sequence, to a supply pressure sensor, thereafter through an inlet fluid line to an inlet port of a cuff bladder, the bladder also having an outlet port coupled to an outlet fluid line of equal length as the inlet fluid line, the outlet fluid line thereafter coupled to a return pressure sensor and an exhaust fluid line, the exhaust fluid line returning the coolant to the reservoir.

A pressure cuff includes an expandable bladder having an inlet and an outlet with a resilient backing material suitable for temporarily enclosing a human limb and the bladder which is affixed to the pressure cuff. The range of volume expansion of the bladder provides for the pressure developed in an enclosed limb to be made substantially equal to the bladder pressure, thereby providing compression and cooling of the limb when a chilled fluid is circulated through the bladder, with the enclosed human limb experiencing a compression equal to the pressure in the bladder and a cooling related to the temperature differential between the limb and the fluid circulating through the bladder.

In another example of the invention for estimating or regulating pressure of a remote bladder, the previously described system is actuated during a first interval until a return pressure is measured and the supply and return pressure sensors provide steady state readings, after which the variable speed pump is turned off, and the supply and return pressures are read when they are substantially equal to each other, from which a head pressure estimate is derived, the head pressure estimate subsequently added to a setpoint pressure, with the system regulating pressure until the setpoint pressure plus the head pressure estimate are substantially equal to the average of the supply pressure sensor measurement and the return pressure sensor measurement.

DETAILED DESCRIPTION OF THE INVENTION

Figure 1:
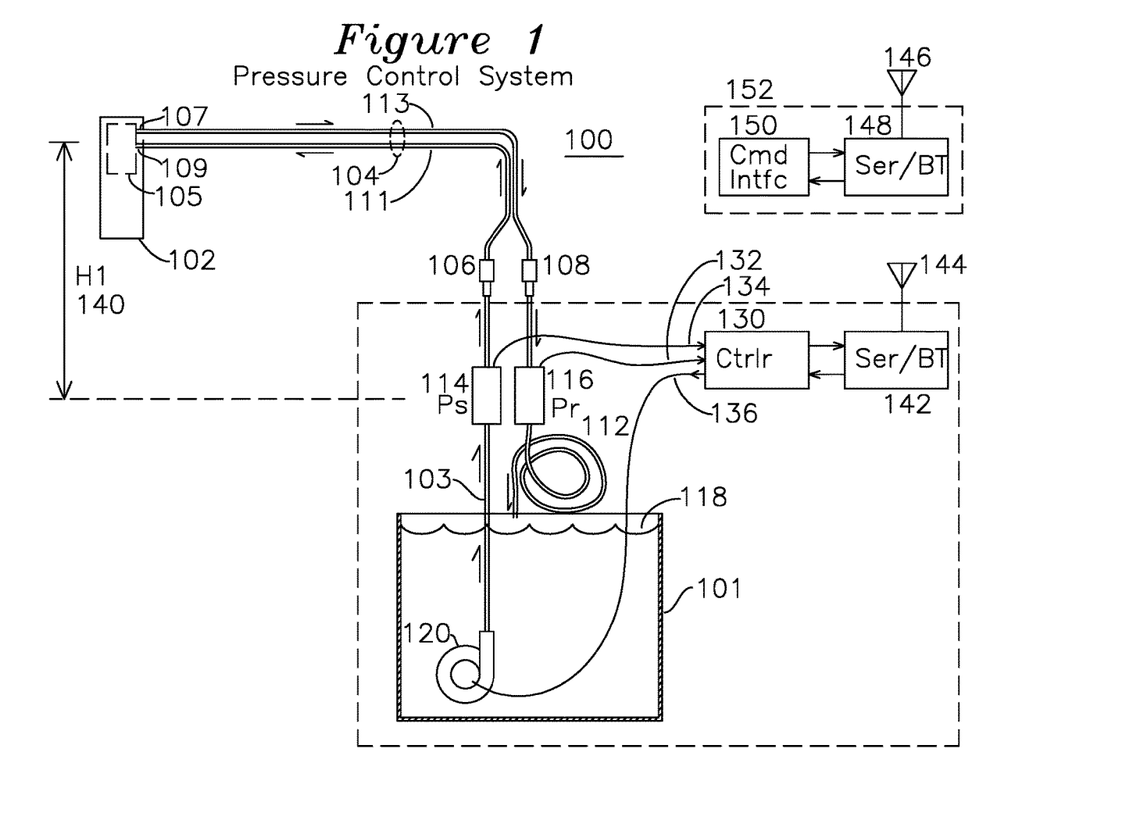
FIG. 1 is a system diagram of a pressure regulation system for a bladder where the bladder is coupled to a reservoir and pressurized through a variable speed pump.

FIG. 1 shows an example of a pressure regulation system 100 according to the present invention. A remote user interface 152 may comprise a wireless tablet which displays a command interface 150 for selection of various operational parameters which is coupled to a wireless interface such as Bluetooth® interface 148 coupled to wireless antenna 146. In one example of the invention, the Bluetooth interface uses the Host Controller Interface (HCI) protocol, which provides serial control such as transmission of control and data as two byte pairs, such as a pressure command byte accompanied by a setpoint value byte which may also be scrambled to maintain synchronization through loss of a command or data byte. The command interface 150 commands are thereafter received by serial/Bluetooth interface 142, which directs pressure setpoint commands along with other commands to the pressure controller 130.

Reservoir 101 contains a circulating fluid such as chilled water 118, which is coupled to a variable speed pump 120 which may be submerged in the reservoir 101 as shown, or placed externally to the tank and coupled to the fluid via a fluid line or hose (not shown). Pump outlet fluid line 103 is coupled to supply pressure sensor 114 which generates an electrical signal 134 indicating measured supply pressure. The supply pressure sensor 114 is coupled through optional removable fluid coupling 106 to a second fluid line 111 to the inlet port 109 of bladder 105 which is part of pressure cuff 102. Bladder 105 may have a fluid circulation path or enclosed region which is coupled to an outlet port 107 which is coupled to third fluid line 113, thereafter to optional removable coupling 108, to return pressure sensor 116 which generates an electrical signal 132, and the return pressure sensor 116 is thereafter coupled to fourth fluid line 112 which returns the circulating fluid to reservoir 101. Upon receipt of a pressure regulation command from the user interface 152 which includes a setpoint pressure, the pressure controller 130 generates a variable voltage electrical signal 136 which is delivered to the variable speed pump 120 to generate a range of pressures suitable to cover the variety of operating conditions and bladder elevations H1 140 required to regulate bladder 105 pressure to the setpoint pressure. In one example of the invention, the controller regulates pressure in the pressure cuff 102 bladder 105 by receiving a requested setpoint pressure from the user interface 152, and compares the setpoint pressure to the measured supply pressure 134 and measured return pressure 132, using an algorithm best understood in examination of FIG. 2.

Figure 2:
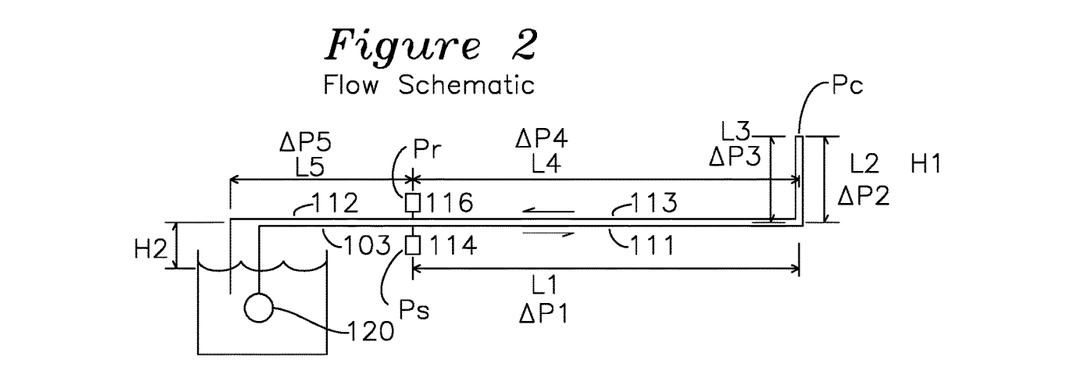
FIG. 2 is a schematic flow diagram of the system of FIG. 1.

FIG. 2 shows a flow schematic diagram for FIG. 1, where the pump 120 pressurizes first fluid line 103 to supply pressure sensor 114, which measures supply pressure Ps. The bladder (having pressure Pc of FIG. 2) is separated from the pressure sensors by a horizontal separation distance L1 plus a vertical separation distance L2, the bladder shown in schematic form as having cuff bladder pressure Pc. The returning fluid travels vertical length L3 and horizontal length L4 and return pressure is measured by return pressure sensor 116. Exhaust liquid travels through a fluid line of length L5 to reservoir 101. Where the sensors 114 and 116 are at the same elevation above the tank water level H2, and when the supply fluid line L1 is of equal length as return fluid line L4, the steady state pressure drop through the fluid lines 111 and 113 are substantially equal, since in equilibrium the flow velocities are balanced and equal (although the pressures in the fluid lines decrease along the path length because of turbulent loss). Additionally, the head pressure contributions of L2 and L3 are offsetting, apart from the flow pressure drops of L2 and L3, which are equal for equal flow velocities due to the matched turbulence pressure loss along 111 and 113, and where the fluid pressure drop (inlet port to outlet port) through the bladder 105 is small compared to the fluid pressure drops through the fluid lines 111 and 113, such as by having open channels in the bladder 105. The bladder 105 having pressure Pc is a height H1 above the pressure sensors 114 and 116, and the pressure sensors 114 and 116 are a height H2 above the reservoir level.

Figure 4:
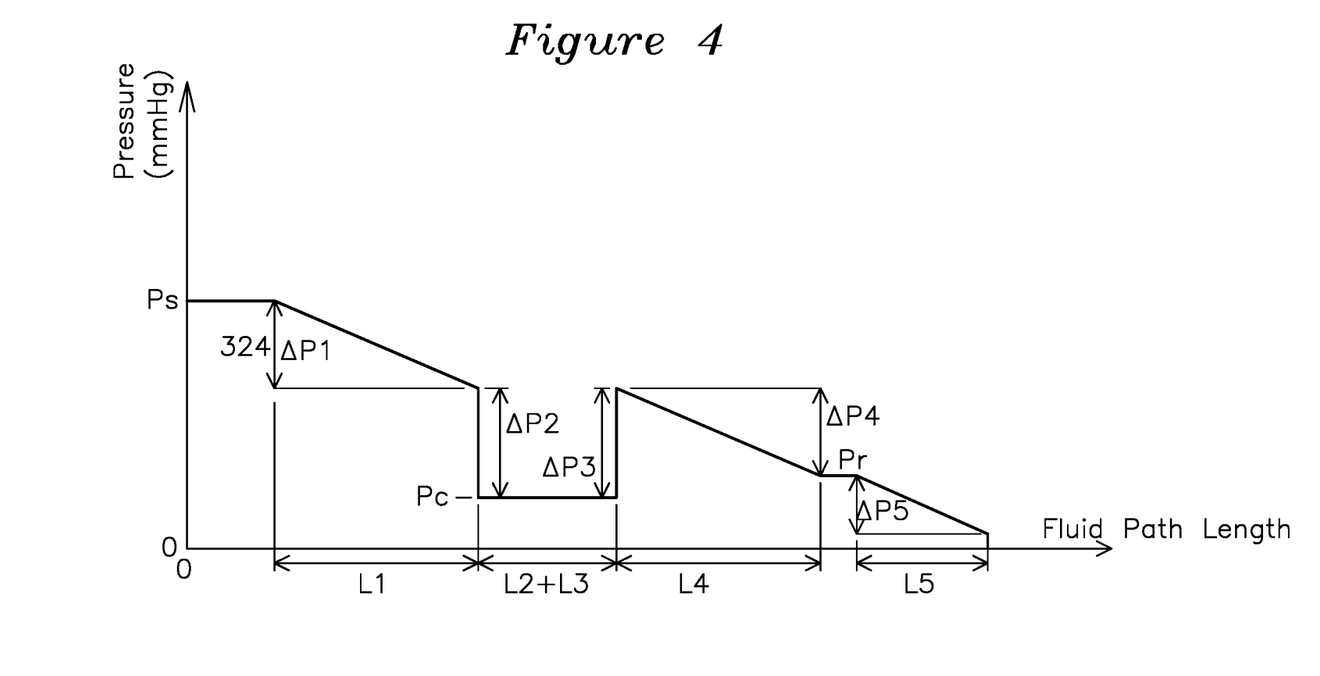
FIG. 4 shows a plot of pressure drops through the fluidic path lengths of FIG. 2.

FIG. 4 shows a plot of the developed pressures along the elements of the system shown schematically in FIG. 2, with the vertical axis indicating the pressure developed at a particular element of the system, and the horizontal axis indicating a particular length of the run. The fluid pressure at the outlet of the pump is shown as Ps, which drops by ΔP1 along the length L1 of the supply fluid line 111, then drops by ΔP2 associated with the vertical change in fluid line 111 over L2, where the bladder pressure is Pc. The subsequent vertical drop of line 113 over L3 regains the pressure ΔP3, which next drops by ΔP4 along L4 of the fluid line 113 to the return pressure indicated as Pr. The final length of fluid line 112 L5 drops the pressure to near 0, as it is near the surface of the reservoir at datum surface level (0) pressure. FIG. 4 is presented for understanding the separate components of pressure drop through the system, it is understood that the fluid lines 111 and 113 of the line set 104 leading to the cuffs will not have strictly vertical or horizontal directional routing from the reservoir to the bladder, although the end to end pressure drop is independent of the fluid line routing but is dependent on vertical height changes and fluid line lengths.

Pressure cuff 102 is preferably designed to encircle a human limb with the bladder 105 on the inner surface of the cuff. As the bladder fills with fluid, it will apply the fluid pressure of bladder 105 to the encircled limb after bladder 105 has filled to the point that additional volume displacement of the bladder 105 translates into a uniform applied pressure in the encircled limb and bladder 105. The cuff 102 encircles the limb and contains the bladder, thereby ensuring that pressure developed in the bladder is in equilibrium with the pressure transferred to the encircled limb. One example of such a cuff and bladder is described in U.S. Pat. No. 8,273,114, which is incorporated by reference. Another example pressurized cuff, also incorporated by reference, is described in U.S. patent application Ser. No. 13/094,799 filed Apr. 26, 2011 with common assignee as the present application.

The steady state operation of the pressure regulation system of FIGS. 1 and 2 may be derived from the below equations. When the cuff 102 bladder 105 is filled and the bladder 105 reaches equilibrium and a steady-state pressure, the inlet and outlet flow velocities are equal, as was previously indicated. In this steady state mode of operation:

$Pc = Ps - \Delta P1 - \Delta P2$ and also $Pc = Pr + \Delta P4 + \Delta P3$.

where:
Pc is the bladder pressure estimate
Ps is the supply pressure from sensor 114
Pr is the return pressure from sensor 116
ΔP1, ΔP2, ΔP3, ΔP4 are the pressure drops as shown in FIG. 2.

Assuming ΔP1=ΔP4 and ΔP2=ΔP3 from the steady state flow condition as previously described, then:

$$Pc = \frac{Ps + Pr}{2} \quad \text{(Equation 1)}$$

The pressure controller 130 may operate according to the equations:

$$Em = \left[K1\left(Pset - \frac{Ps+Pr}{2}\right) + K2 \int\left(Pset - \frac{Ps+Pr}{2}\right)\right] \quad \text{(Equation 2)}$$

where
Em=voltage applied to a the DC motor of variable speed pump 120;
Pset=setpoint pressure;
K1 is a gain constant for a first term which is proportional to the error term;
K2 is a gain constant for a second term which integrates the error term to greatly reduce static offsets.

A controller which operates according to Equation 2 may also be referred to as a PI (proportional/integral) feedback control system. The generalized form is a PID (proportional/integral/differential) controller, although the inventors have found little benefit from the addition of a derivative error term in favor of the proportional error term and integral error term components of the error for use in generation of a correction voltage applied to the pump motor. One difficulty of using a differential term in feedback is that the bladder tends to be elastic, which adds a non-linear open loop characteristic to the system, causing instabilities at low pressures where the open loop gain tends to be higher because of this nonlinearity than at low pressures where the elastic expansion of the bladder is lower. The removal of the differential feedback term improves the consistency of the closed loop response over pressure ranges, and the use of an integration constant K2 which is less than 2% of the full scale range of the pressure value removes static offset errors between setpoint and measured pressure, thereby allowing a range of K1 values which are multiples of 16 or more of the K2 value, while still providing favorable closed loop response.

Figure 3:
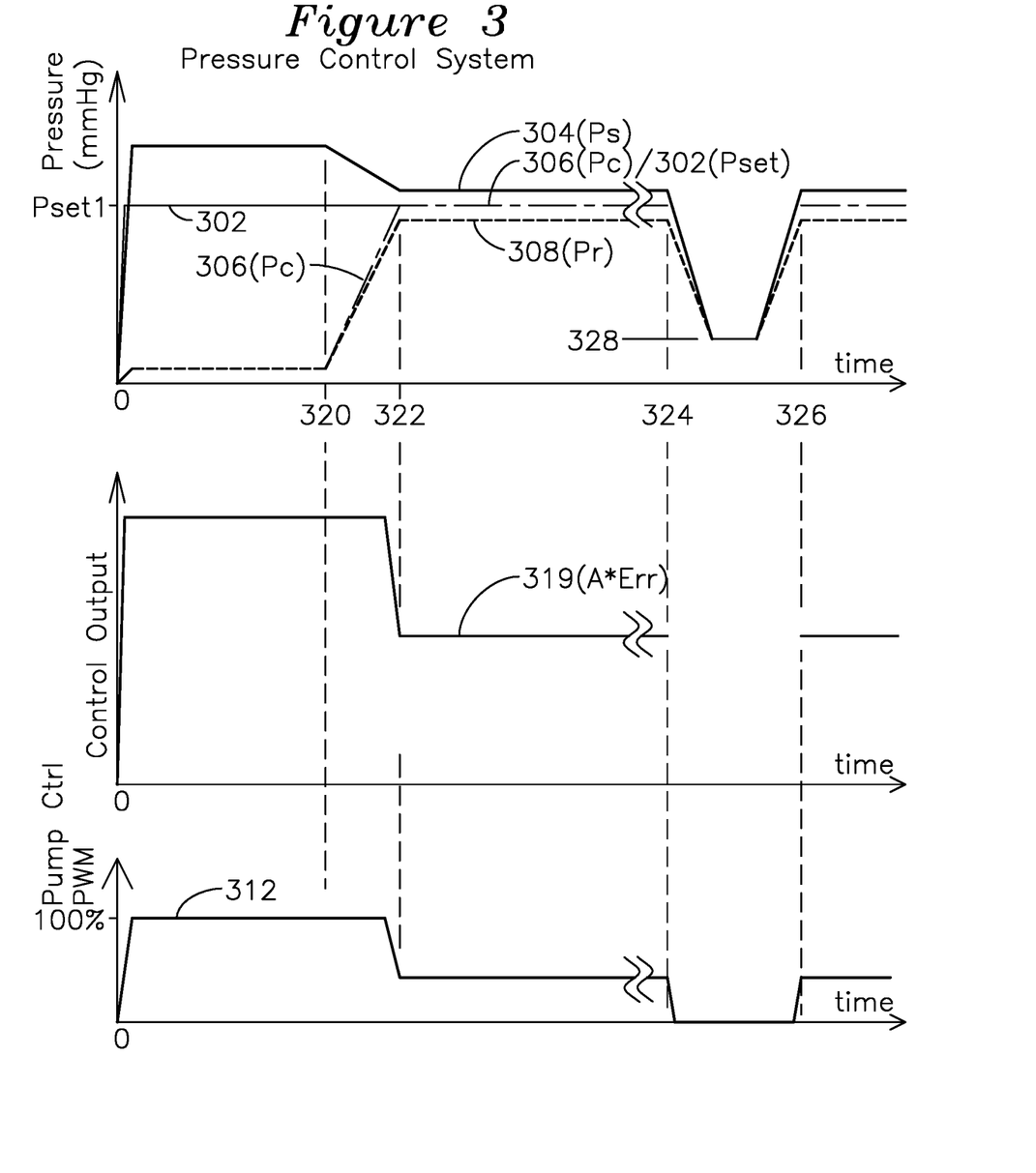
FIG. 3 shows pressure plots for operation of the system of FIG. 1.

FIG. 3 shows time-domain plots for the operation of the system starting from a rest state with a deflated or empty bladder 105 (associated with plot Pc 306) and the pump 120 (associated with plot 312) off. Setpoint 302 Pset starts at setpoint 0 mmHg and time 0, as does supply pressure Ps 304, return pressure 308, and with pump pulse width modulation (PWM) at 0 since the error signal is also at 0 since the setpoint is 0 at starting point 320. The pressure setpoint 302 ramps to Pset1, which causes a large error signal 319 through time 320 and ramps to a desired setpoint pressure 302, which is converted into pump PWM 312 going quickly from 0 mmHg at time 0 to 100% duty cycle through time 320. The supply pressure sensor generates estimate Ps which generally follows the pump PWM output, as shown by comparing PWM curve 312 to Ps 304. As the bladder fills and inflates, bladder outlet flow initiates and return flows increase in the return fluid lines (113 and 112 of FIG. 1), causing the return flow pressure Pr 308 to ramp up until a steady state flow condition is reached at time 324, where the midpoint between Ps 304 and Pc 308 represents an accurate estimate of bladder pressure Pc 306 where the height difference L2 is negligible. In the case where L2 is a significant source of pressure offset (referred to as head pressure), this pressure may be added to the setpoint pressure, effectively placing the pressure sensors 114 and 116 at the same elevation as the cuff bladder 105. The technique of adding bladder elevation to the setpoint pressure to compensate for elevation differences between the cuff and the pressure sensors is useful where the bladder elevation is known and well controlled.

Figure 5:
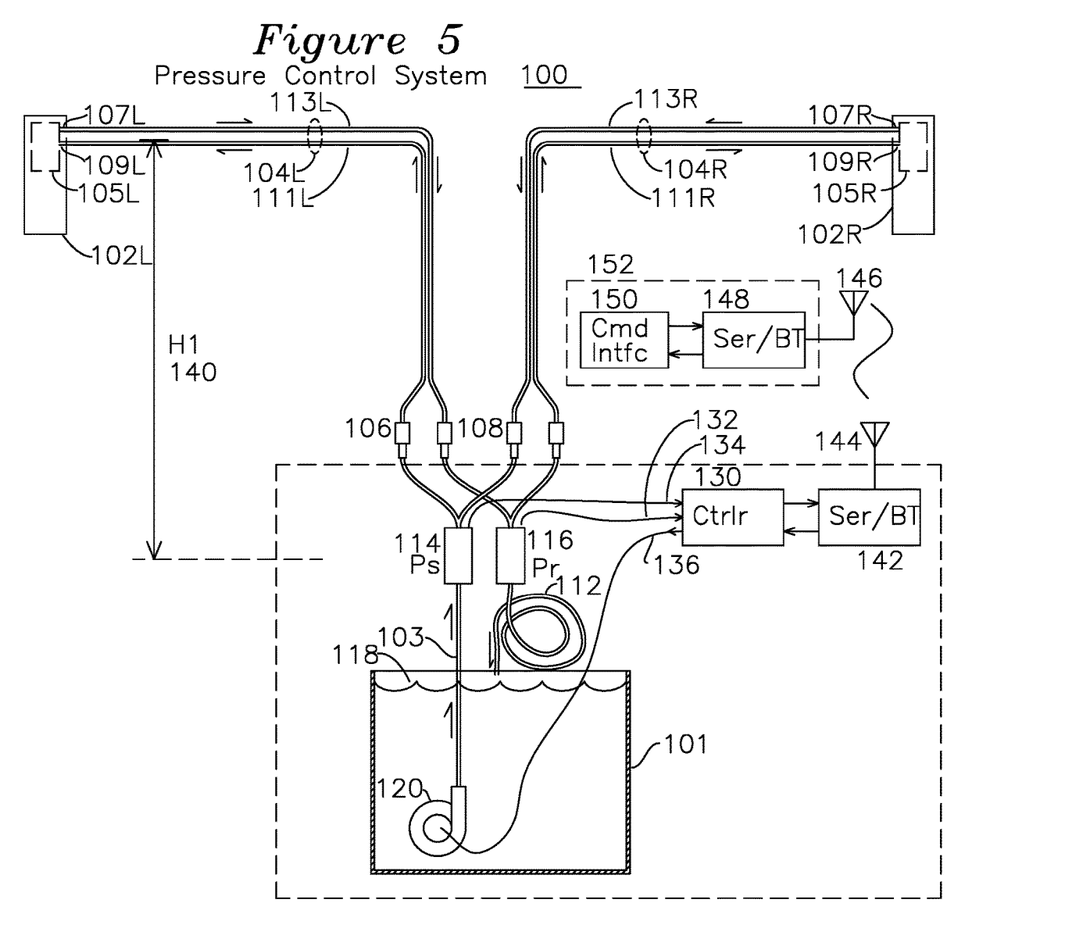
FIG. 5 shows a system diagram for a two-cuff example of the system of FIG. 1.

FIG. 5 shows the system of FIG. 1 adapted for the example of a two cuff system having left cuff 107L and right cuff 107R, with equal length second fluid lines 111L and 111R and equal length third fluid lines 113L and 113R. The other associated elements of the two cuff system of FIG. 1 shown in FIG. 5 have L and R suffixes, with the supply pressure sensor 114 output splitting off into the two supply lines 111L and 111R, and the return pressure sensor 116 operative on the combined return lines 111L and 111R. The system of FIG. 5 is suitable for application of a pair of cuffs to the arms or legs of a human subject for application of pressurized cooling, with the arms and legs receiving a different head pressure compensation. Such a pressurized cooling system is described in U.S. Pat. No. 8,273,114. A second set of pumps and controllers may also be used with reservoir 101 to similarly provide pressurized cooling for the legs of a user, with the controller 130 operative for an arm pressure setpoint, with associated head pressure offset, which is distinct from a leg pressure setpoint and associated head pressure offset.

Another important and unexpected feature of the system of FIG. 5 is the characteristic that the pressure regulation system continues to operate accurately when the lengths of 113L/111L and 113R/111R cuff lines are different. The cuff pressures developed in bladder 105L and 105R will be equal even though the lines 113L/111L are shorter or longer than lines 113R/111R. This feature provides increased flexibility in the design of cuffs and associated lines, as well as the manufacturing and deployment of the cuffs and connecting fluid lines. As equation 3 indicates, the requirement for equal length left fluid lines pair 104L and right fluid line pair 104R is not critical—for a wide range of length of these fluid lines, the cuff pressure at each remote cuff will be the average pressure of Ps and Pr (ignoring head pressure H1, which may be compensated as a pressure offset as described previously). The other referenced elements of FIG. 5 operate as was described for the reference numerals of FIG. 1. In a typical configuration, the datum reference for H1 is at the elevation of pressure sensors 114 and 116, which are at the same height. In an alternative embodiment, pressure sensors 114 and 116 are at different elevations, and in this case, the datum point is the midpoint elevation of pressure sensors 114 and 116.

Figure 6:
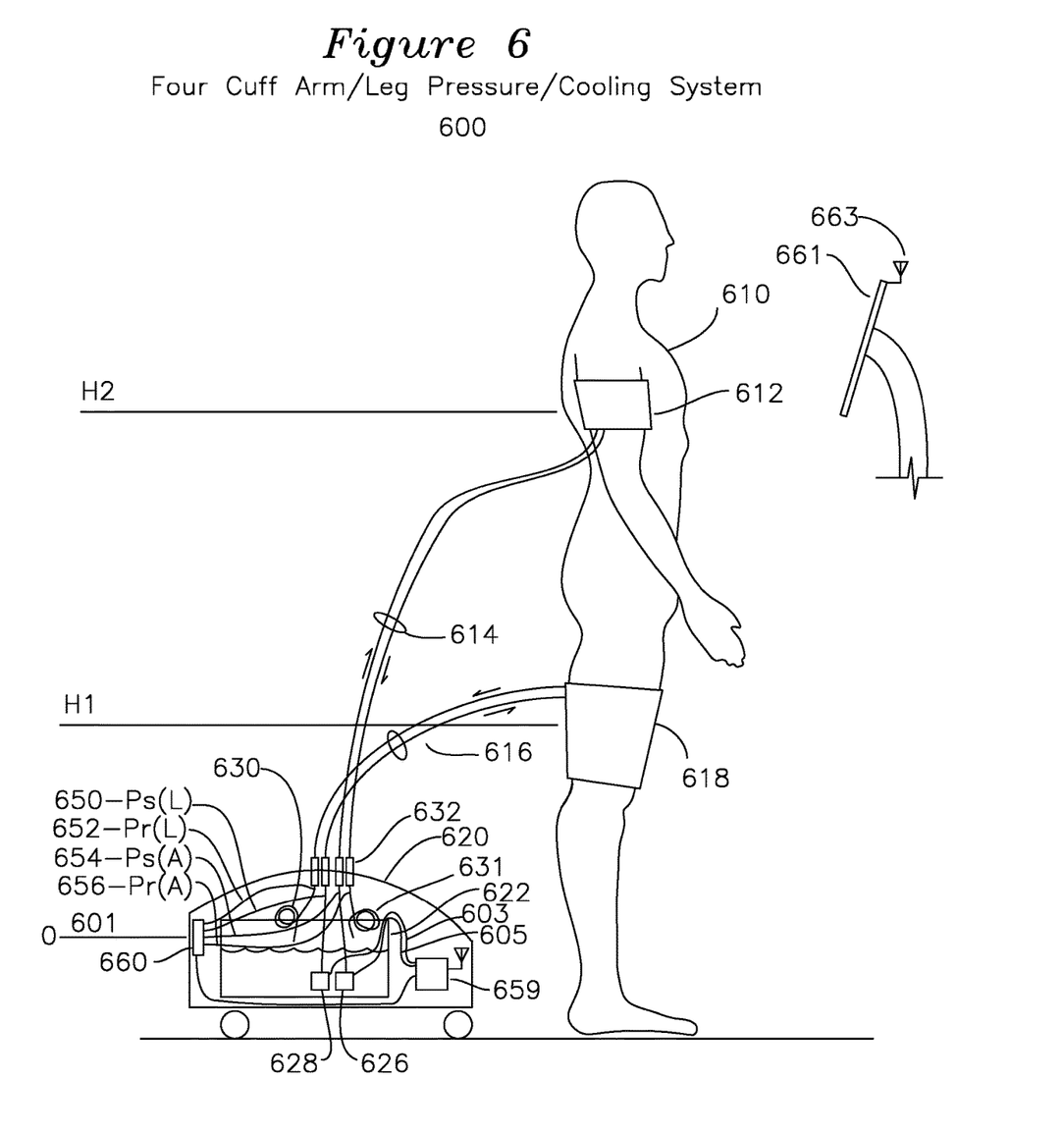
FIG. 6 shows an example pressure cooling system having two pressure regulated arm cuffs and two pressure regulated leg cuffs with cuff height head pressure compensation.

FIG. 6 shows a system 600 for arm and leg cooling and compression according to the present invention. An exercising subject 610 (exercise machine not shown) operates a user interface 661 such as a tablet computer which enables the selection of arm pressure setpoint and leg pressure setpoint, which are communicated via the Bluetooth protocol over wireless antenna 663 to pressure control interface 659 which comprises wireless interface and pressure controller 130 of FIG. 5 as previously described. The example system of FIG. 6 has a pair of arm cuffs 612 (one of two are shown for clarity) and a pair of leg cuffs 618 (one of two are shown for clarity), with the arm cuff pair connected via fluid lines 614 to quick release couplings 632, and the leg cuff pair connected via fluid lines 616 to quick release fittings 632. The quick release fittings 632 enable convenient separation of the cuff lines 614 and 616 from the pressure regulation coolant/pressure delivery system 620. As was described previously, the arm pressure regulation system operates independently from the leg pressure system, with the arm cuffs having a head pressure compensation distance H2 above the pressure sensor assembly 660, and the leg cuffs having a head pressure compensation distance H1 above the pressure sensor assembly 660, which may enclose the arm supply pressure sensor coupled to line 654, the arm return pressure sensor coupled to line 656, the leg supply pressure sensor 650, and the leg return pressure sensor coupled to line 652 and delivers those pressure measurements to pressure control interface 659. Accordingly, arm pump 626 is driven by controller output and generates a supply pressure for arm cuff 612 which setpoint includes the head pressure offset H2, and leg pump driven by controller output 603 generates a supply pressure for leg cuff 618 which setpoint includes a head pressure H1 above pressure sensors 660. The pressure regulation system operates on the error term derived from the difference between setpoint and average supply and return pressure is used to form a motor control signal in the form of a pulse width modulation (PWM) of a DC voltage which varies from 0% duty cycle to 100% duty cycle. This signal has the effect of efficiently providing control of motor speed, and may be applied to motors 626 and 628 by their respective control and estimation systems, as was previously described. The distances H1 and H2 are with respect to the 0 datum of the pressure sensors 660, and are unrelated to the fill level of the reservoir 622. Arm return line 631 is shown as coiled, as is leg return line 630, which provides back pressure and flow resistance for the arm return pressure and leg return pressure sensors, respectively. Return lines 631 and 630 may be selected for inner diameter or length to provide a pressure drop in the range of 10% to 30% of the maximum pressure provided by the respective arm pump 626 and leg pump 628 at an operation flow rate which may be in the range of 2 to 20 gallons per hour (GPH), nominally 4 GPH, or where the source pressure varies from 2 pounds per square inch (psi) (nominally mmHg) to 6 psi (nominally 300 mmHg) at 0 GPH flow rates, the maximum pump head pressure operating point. Higher pump pressures or flow rates may also be used. The development of back pressure may be helpful for increased delivery of pump pressure to the cuff for pressurization of the cuff, as well as the placement of the pump motor operating characteristic in an optimal pump control range for desired pressures to be developed in the cuffs. In one example of the invention, the return fluid line 112 of FIG. 1 is selected to provide back pressure at the return sensor 116 in the range of 25% to 50% of the pressure developed at the source pressure sensor 114, although it may vary from 10% to 80% of the source pressure. For good dynamic range control, it is typically desired in a PWM control system to operate in the range of 25% to 50% duty cycle in steady state regulation, such that, in an example of operation of the system of FIG. 1 and with 4 GPM of flow through a single cuff 102 bladder 105, a pump 120 may operate in the range of 150 mmHg (20 kPa or 2.9 psi) pressure delivered to a supply sensor 114, experience a pressure drop of 37.5 mmHg (5 kPa, or 0.725 psi) along each flow path 111 and 113, and provide a pressure drop of mmHg (10 kPa or 1.45 psi) across the return fluid line 112, thereby providing a measured return pressure 116 of 112.5 mmHg (15 kPa or 2.17 psi), less the head pressure drop associated with elevation H1. For H1=24" (609 mm), the resultant pressure reduction from the elevation of the cuff above the sensors would be 44 mmHg (5866 Pa, or 0.85 psi), and the pressure at the bladder 105 would be 112.5 mmHg less mmHg, or 68.5 mmHg (9.132 kPa or 1.32 psi) delivered to the arm (or leg) enclosed by arm (or leg) cuff 102.

A method of determining the offset head pressure H1 of FIG. 2 directly from the in-use setup which accommodates a wide range of H1 bladder height is available in the examples of FIGS. 1 and 2 using a dynamic method shown in the time interval from 324 to 326 of FIG. 3. The pump motor may be run until a return pressure is sensed at time 322, or until equilibrium is reached at time 324. The pump is next turned off at point 324 until the measured supply pressure and measured return pressure provide only head pressure 328. This may be done after the pump shutdown and source pressure drop, with the duration from 324 to 326 governed by the dynamic behavior of Ps 304 and Pr 308, which will initially converge on a common pressure estimate 328 and hold this pressure during the interval of time between 324 and 326 when the bladder inlet and outlet are both draining. Subsequently, this head pressure estimate 328 may be used to modify the setpoint pressure to provide a compensated setpoint pressure for bladder 109 which accommodates the particular height H1, such that the average pressure of supply pressure sensor 114 and return pressure sensor 116 is now set to the setpoint pressure plus the head pressure developed by H1 and the bladder 107 pressure is now regulated to the setpoint pressure which includes elevation offsets of the cuff. The pump may be restarted and pressure regulation resumed immediately after the head pressure estimate is made, as shown in FIG. 3 at time 326.

Figure 7:
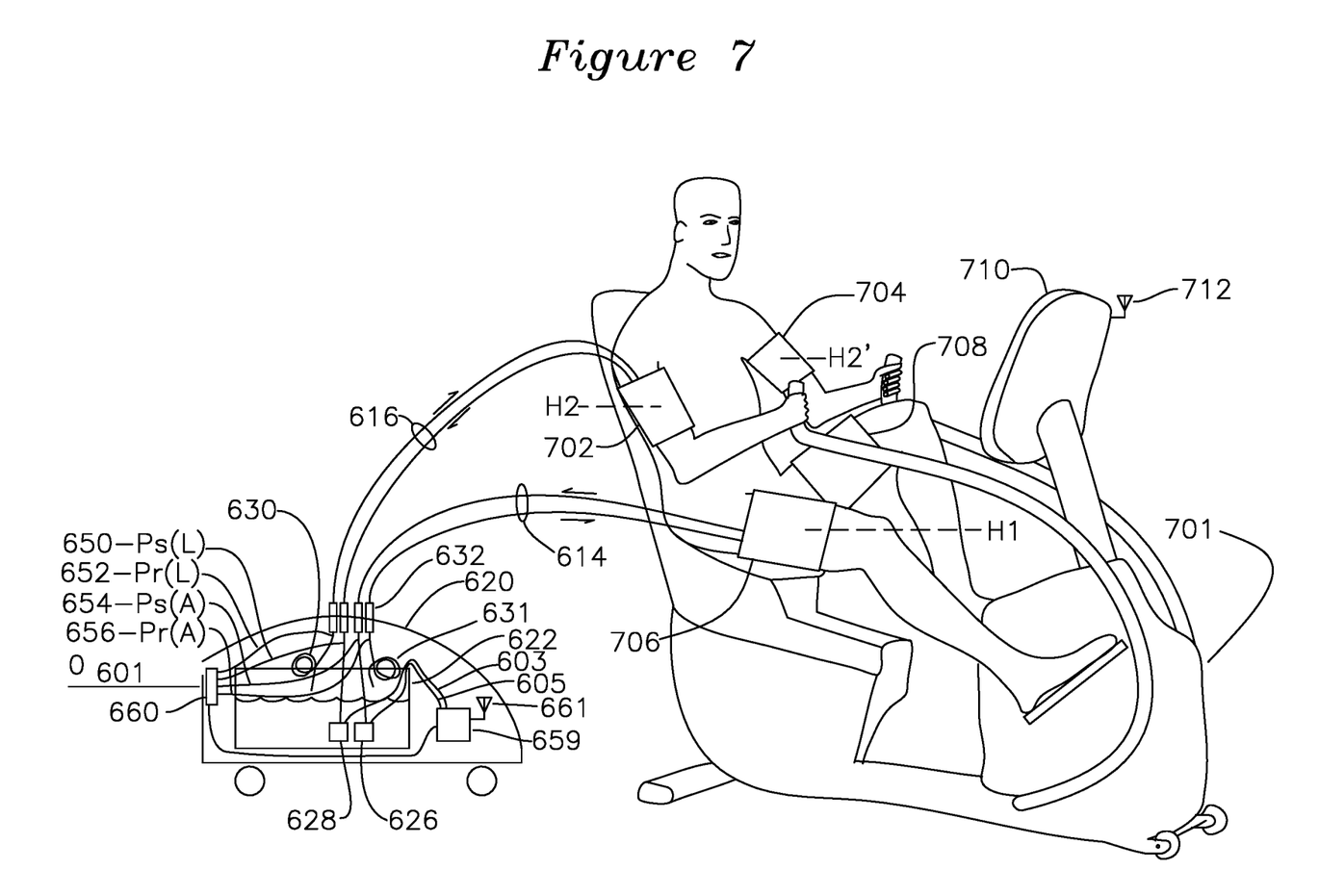
FIG. 7 shows an example pressure cooling system in use with a wireless user interface coupled to a controller.

FIG. 7 shows another example of the compression cooling system in use with an exercise bicycle 701, which may include arm cuffs 702 and 704 at height H2 above the pressure measurement datum 601. Leg cuffs 706 and 708 are at height H1 above pressure measurement datum 601, and a user interface 710 may provide exercise protocols which have programmable resistance levels.

Figure 8:
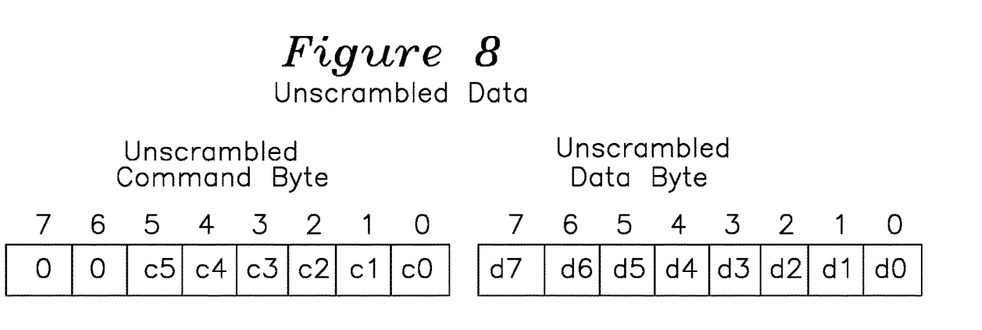
FIGS. 8 and 9 show an example scrambling and unscrambling of control and data bytes for improved communication reliability.
Figure 9:
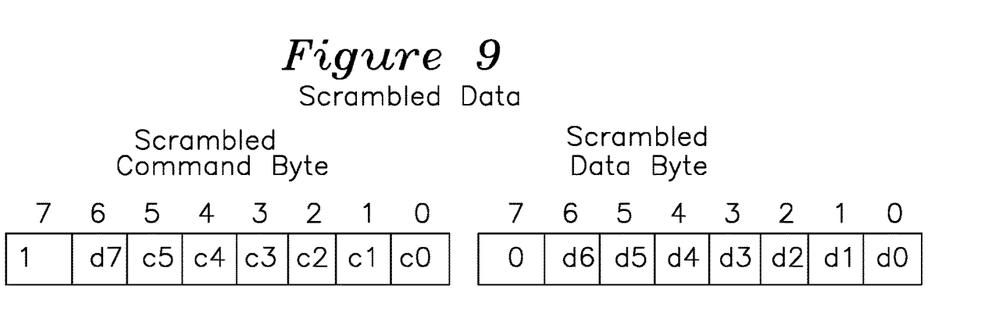

As described previously, the user interface 152 of FIG. 1, such as wireless tablet 661 with antenna 663 of FIG. 6, and wireless tablet 710 with antenna 663 of FIG. 7 generate various commands to pressure controller of FIG. 1 (and associated pressure controllor control interface 659 of FIGS. 6 and 7), where the commands are read commands (such as a pressure sensor read operation) or write commands (such as a pressure setpoint write command). Because the Bluetooth HCI interface encodes and decodes these commands as an unframed serial data stream, it is important that each command be issued in a way that can be unambiguously decoded and unambiguously acknowledged as having been received. FIGS. 8 and 9 show an example method for accomplishing this. Read and write commands are encoded into command bits c0 to c5, with associated read or write data d0-d7. The scrambling method of FIG. 9 shows that the result of scrambling the bits of FIG. 8 command/data byte pair is a remapping such that the most significant bit 7 (MSB) of the command byte is always 1, and the most significant bit 7 (MSB) of the data byte is always 0, with the data bit d7 placed into the scrambled command byte, as shown in FIG. 9. This remapping provides the functionality that a two-byte command/data pair is distinguishable for command and data such that loss of synchronization through loss of a byte is detectable. Descrambling occurs in the reverse order, which restores scrambled data received in FIG. 9 to its original form of FIG. 8.

Figure 10:
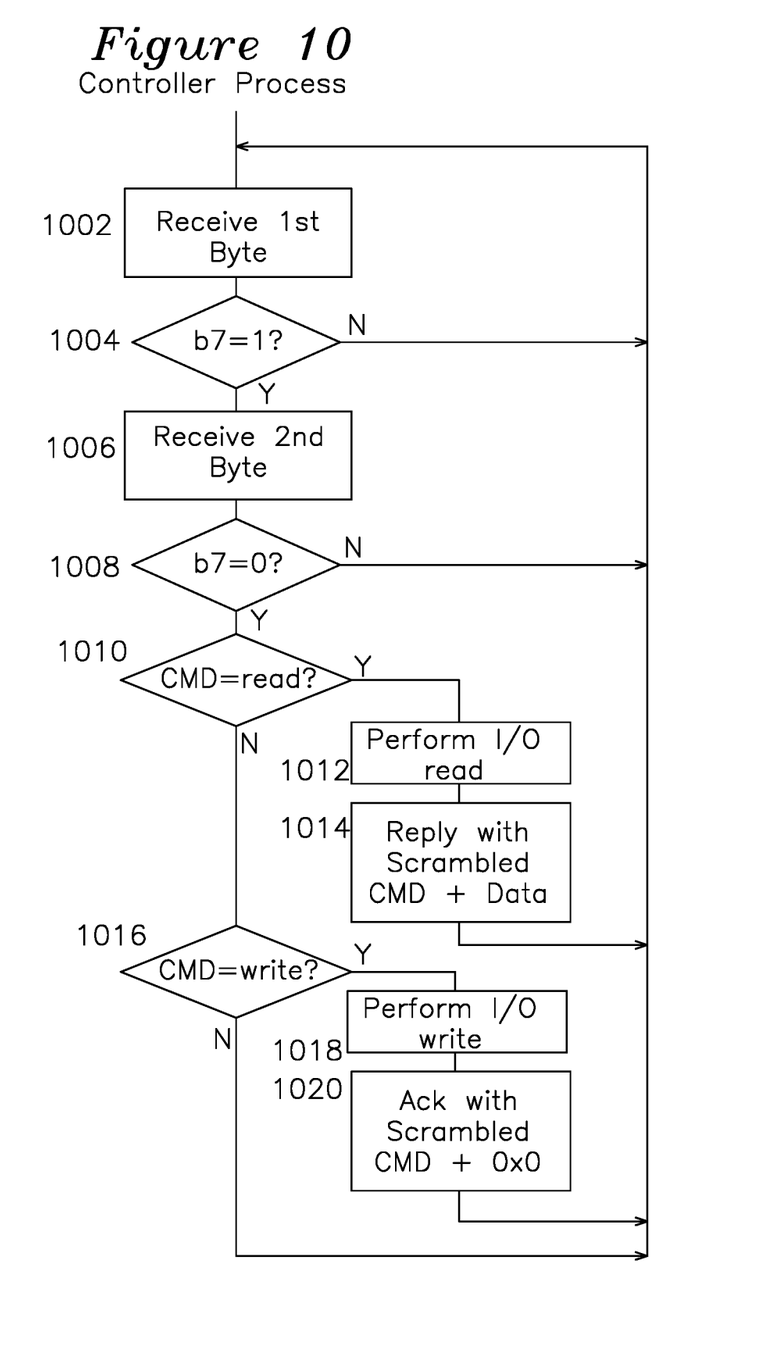
FIG. 10 shows a flowchart for a communication process for a controller.

FIG. 10 shows the controller process for a pressure controller (such as 130 of FIG. 1) receiving and responding to two-byte instructions (command data) from a user interface (such as 152 of FIG. 1). In step 1002, the controller receives a first byte (which may be a proper command byte or an out-of-sync data byte). Step 1004 tests the MSB to determine if it is a command byte, and if so, the second byte is received 1006 and tested to verify the MSB is for a data byte 1008. A failure to match in steps 1004 or 1008 indicates a loss of Command/Data synchronization, and results in a return to step 1002. A read command 1010 (such as a READ_ADC0 for a pressure sensor analog to digital converter read operation) results in the associated 10 operation being performed 1012, which is acknowledged by returning a two-byte reply being the scrambled command and scrambled read data from the read operation. If the received command is a write operation 1016 (such as write data to pulse width modulation (PWM) register for pump 0), the write operation 1018 is performed, and an acknowledgement is returned in the form of the scrambled command with data set to value 0. In this manner, all commands to the controller are two bytes (a command byte and a data byte), and all acknowledgements are also two byte operations, comprising a command byte (with MSB=1 and which is identical to the scrambled command sent by the UI) acknowledgement followed by a data byte (with MSB=0).

Figure 11:
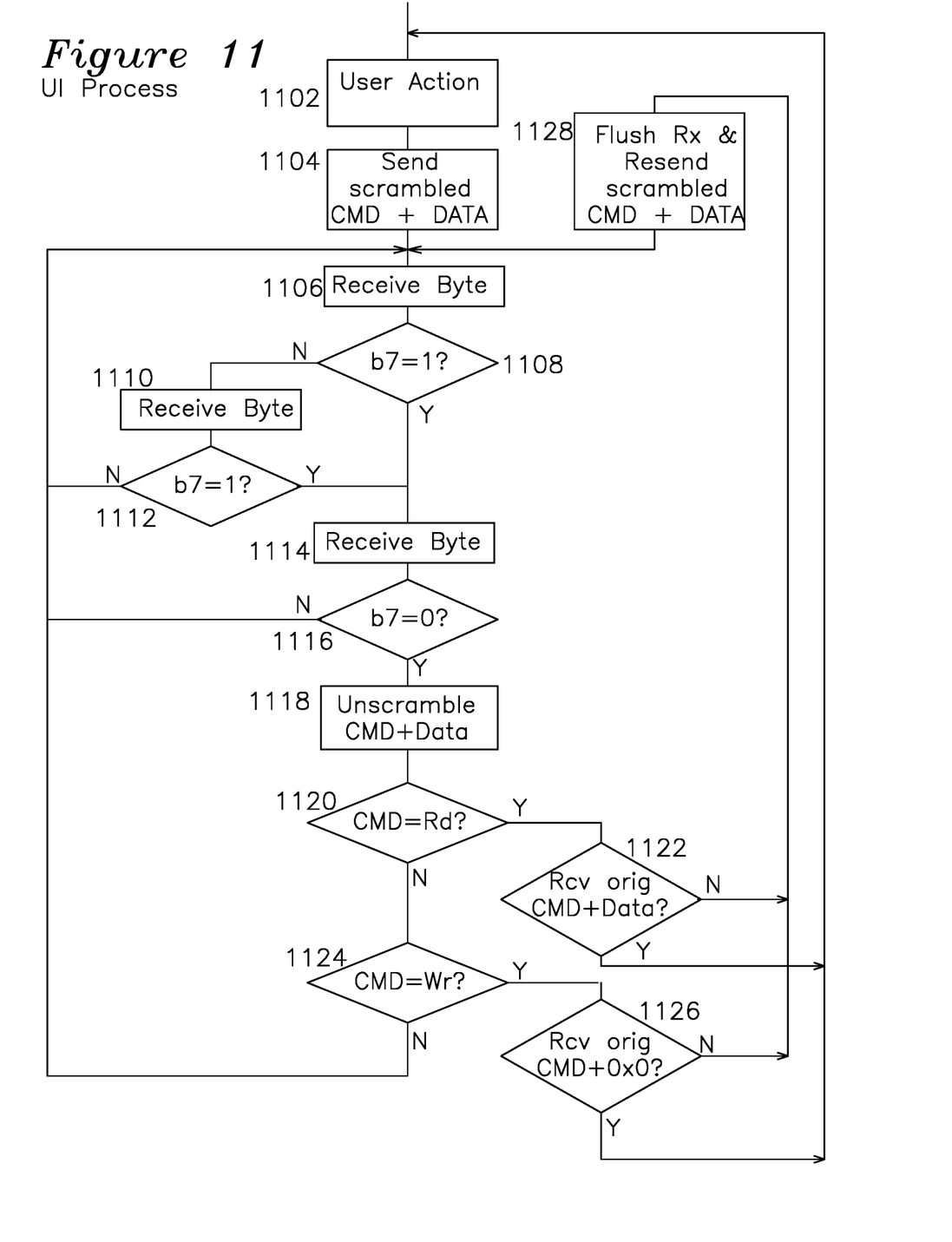
FIG. 11 shows a flowchart for a user interface process for use with the communication process of FIG. 10.

FIG. 11 shows a corresponding User Interface (UI) process for use with the controller process of FIG. 10. The user interface process responds to a user action by issuing a corresponding command to the controller operative on the process of FIG. 10, which responds by either returning the requested data of a read command (such as a pressure read operation) or acknowledging the success of a write command (such as a temperature setpoint command). A user action 1102 results in the sending of scrambled command and data 1104 (generated as shown in FIG. 9 from the command/data pair of FIG. 8), after which an acknowledgement from the controller (FIG. 10 steps 1014 or 1020) is received, the acknowledgement comprising a scrambled command byte (tested in step 1108) and a scrambled data byte (tested in step 1116). If the command/data pair received from the pressure controller 130 is proper, the pair is unscrambled in step 1118 as was described for scrambled command/data of FIG. 9 to unscrambled command/data of FIG. 8. If the command is a read operation responsive to an originally sent read command in step 1104, the associated unscrambled read data of the read command is received 1120 and used by the UI process, otherwise the receive buffer is flushed and the command re-transmitted in step 1128. If the command previously issued in step 1104 was a write operation 1124, the originally sent command of step 1104 is compared with the acknowledgement received in step 1126, and the acknowledgement data for a write command of 0x00 is also verified. If there is a failure of acknowledgement, the receive buffer is flushed and the original command and data are scrambled and resent in step 1128. In this manner, read commands and write commands may be sent from the UI to the pressure controller and acknowledged along with any data exchange. Examples of read commands are read operations for each of the pressure sensor ADCs. Examples of write commands are writing various registers of the pressure controller, such as enabling a channel of the pressure regulator, issuing a regulation setpoint, or directly writing to a PWM register for an associated motor driver (such as a channel which is operating open loop against a written PWM value, rather than regulating to a particular setpoint).

Figure 12:
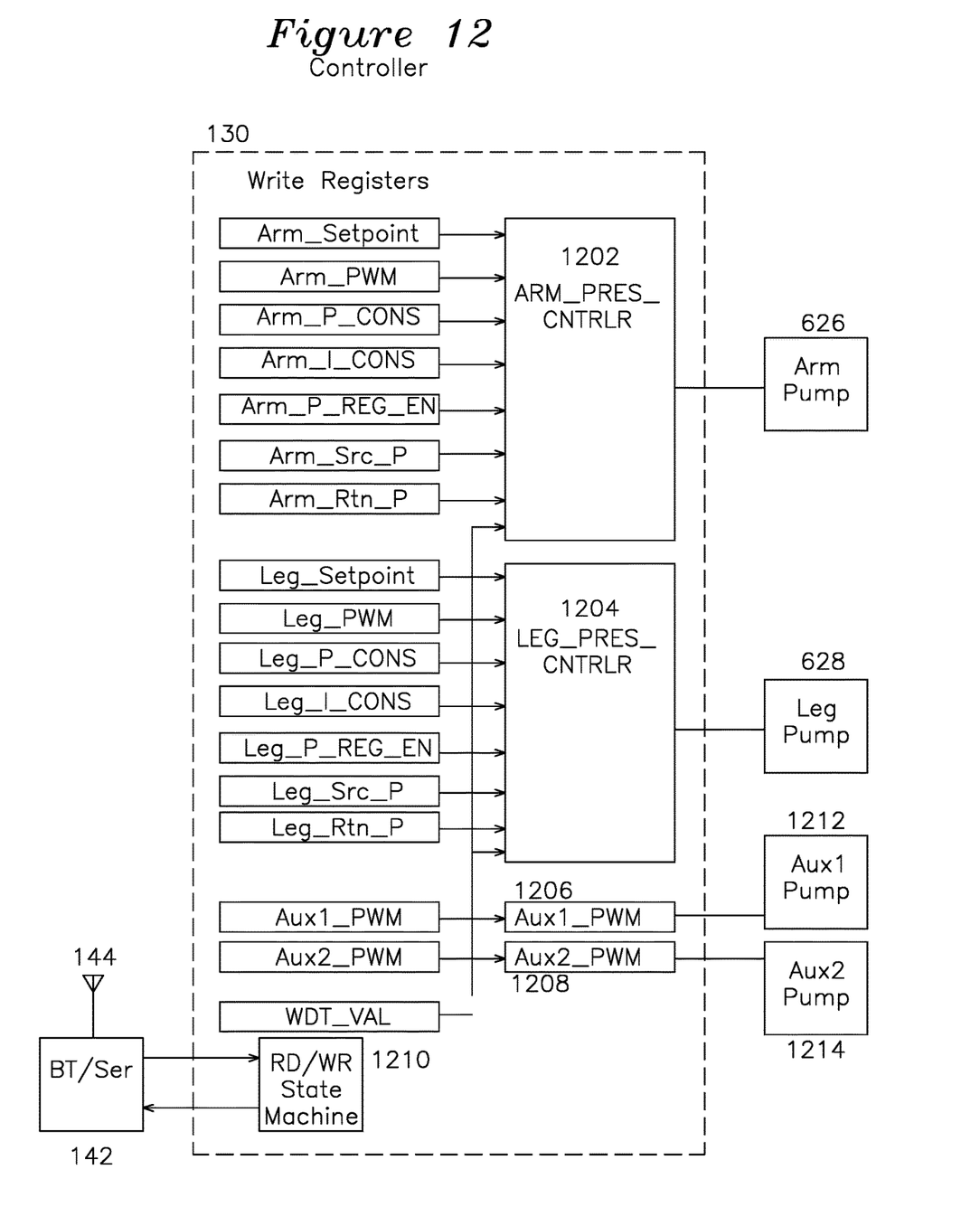
FIG. 12 shows a block diagram for an example controller.

FIG. 12 shows an example pressure controller 130, which may have an arm pressure controller 1202 and a leg pressure controller 1204, both of which regulate pressure to a setpoint pressure as described earlier. Additionally, a first auxiliary PWM 1206 and a second auxiliary PWM 1208 may be used to set a pump to a particular PWM value or speed through a voltage setting which does not perform pressure regulation, but operates to generate a variable pump speed by application of a pump voltage or PWM duty cycle percentage, as is known in the art. Such PWM channels may be useful for controlling the flow and rate of cooling of wearable vests or foot plates during exercise. The controller 130 is accessible via Bluetooth antenna 144 and Bluetooth to serial adapter 142, which passes command/data pairs to the read/write state machine 1210 which may operate using the controller process described in FIG. 10. Each pressure regulation controller 1202 and 1204 has a series of input values which are programmed through the Bluetooth interface 142 and are stored in registers using the command/data pairs as previously described. Example registers for operation of the arm pressure controller 1202 include a setpoint register (Arm_Setpoint) for setting a regulation pressure, a PWM register (Arm_PWM) register for optional open loop control using only PWM rather than pressure regulation, a P_constant register (Arm_P_CONS) and I_constant register (Arm_I_CONS), both of which are used to store feedback control parameters used by the pressure controller 1202, a regulation enable bit (Arm_P_REG_EN) used to start and stop the pressure regulator 1202, and the stream of ADC values for the supply and return pressures (ARM_Sup_P and Arm_Rtn_P) which are read and used to perform real-time pressure regulation. With respect to the components shown in FIG. 6, the arm pressure regulator 1202 drives arm pump 626, the leg pressure controller drives the leg pump of FIG. 6, and the two auxiliary PWM controllers 1206 and 1208 drive auxiliary pumps 1212 and 1214 for use in auxiliary cooling panels (not shown) which do not regulate pressure, but are useful for controlling flow rate through such auxiliary cooling panels and thereby providing a user control for rate of cooling. The WDT_VAL register of FIG. 12 is a watchdog register which is initialized and then counts down to 0 over a duration of time equivalent to a fraction of a cuff fill time, such as 0.25 seconds to 2 seconds for a cuff fill time of 15 s, at which time it causes all of the pressure controllers 1202 and 1204, and PWM controllers 1206 and 1208 to reset, thereby causing all of the pumps in the system to stop developing pressure. The WDT_VAL register must be periodically overwritten with the timer value by the user interface, which is useful for preventing a condition where a loss of connectivity to the user interface 152 would otherwise cause the pressure regulators 1202 and PWM controllers 1204 to continue without connectivity to the user interface 152, as well as circumstances where the user interface 152 program may crash or lose power.

Figure 13:
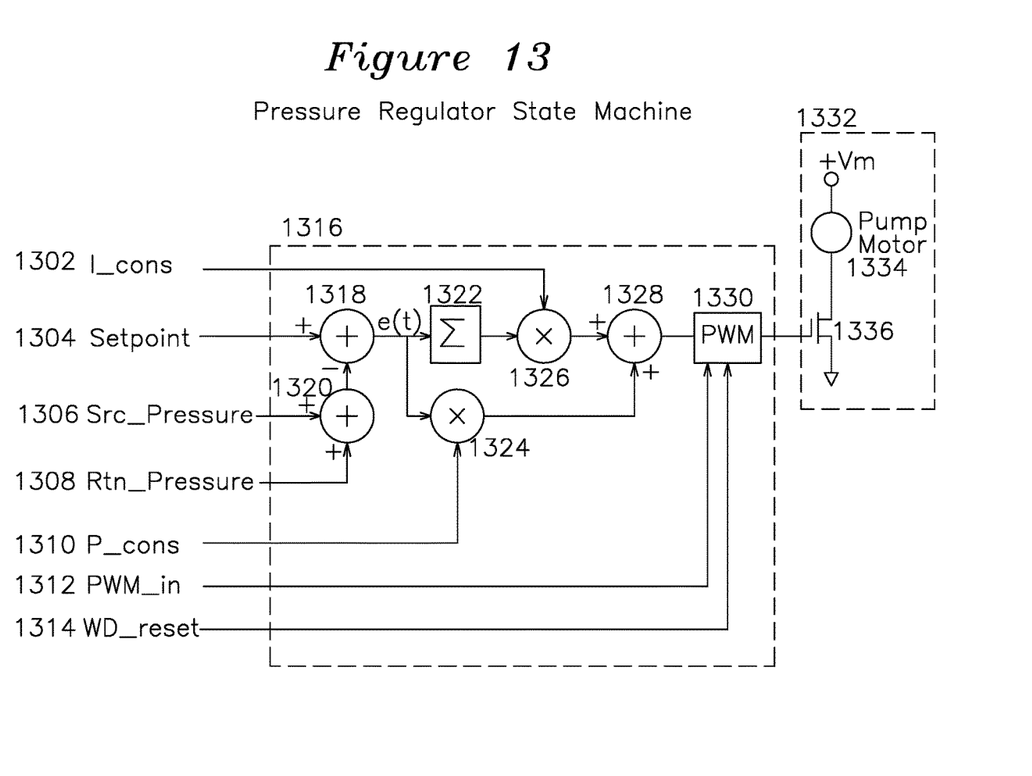
FIG. 13 shows an example digital pressure controller for controlling a variable speed pump to a setpoint pressure using PWM.

FIG. 13 shows an example digital pressure controller 1316 such as 1202 or 1204 of FIG. 12. Supply pressure and return pressure inputs 1306 and 1308 are added 1320 to form a sum which is subtracted 1318 from the setpoint value. Note that the sum is not divided by two (such as by truncation of 1 bit) of equation 1 above, as it is preferable to preserve the resolution of the measured and computed intermediate values, and to scale the setpoint accordingly, in this example by left shifting the binary setpoint value by one bit position. Typically, the inputs 1306 and 1308 are digitized voltages from an ADC, and setpoint 1304 is a static value of the previous setpoint pressure which was selected. The output of adder 1318 is an error term e(t), and a first term is formed by multiplication of a proportional constant P_cons 1310 with e(t) and a second term is formed by integration 1322 of e(t) and multiplication by I-cons 1302. The first and second terms are added together 1328 and delivered to a PWM 1330, which is resettable by WD_reset 1314, or alternatively may be controllable directly by PWM in 1312 where flow control by writing a PWM value to the pump motor is needed rather than pressure regulation. The output of the PWM 1330 may be applied to a switch element such as Field Effect Transistor (FET) 1334, thereby effectively providing a continuously variable pump control voltage to pump motor 1336 without dissipation of heat in switch 1334. Any equivalent switchable component may be used for switch 1334, including semiconductor devices, optically actuated devices, field effect transistors, or bipolar junction transistors.

The examples of the system and components are for understanding the invention only, and do not limit the invention to the particular examples shown. For example, the pumps may be direct current (DC) pumps which are controlled by a variable DC pump control voltage, or the pumps may be DC pumps which are provided with a fixed DC voltage which is switched on and off with a duty cycle, thereby providing a pulse width modulated (PWM) equivalent voltage of the present example. Where the PWM duty cycle varies from 0 to 1, the output voltage switching between 0V and Vsupply volts, the effective DC pump motor voltage (Veffective) will be Veffective=Vsupply*PWM. Rather than changing pulse width with a fixed pulse repetition rate to accomplish PWM, it is also possible to change the pulse repetition rate for a fixed pulse width, or any other method known in the art of motor speed control. When a PWM system is used, a low loss element such as a field effect transistor (FET) may be used to minimize switching losses and resistive losses. Alternatively, the pumps may be an AC pump with a variable frequency drive, or any other drive type which provides variable speed operation. The pump may be run at constant speed and throttled using a valve, all of which are understood to be a variable speed pump motor controlled by a pump control voltage as understood in the present specification.

The term "substantially" is understood in the present specification to mean within the limits of +/−20% of the referenced pressure, length, diameter, height, or voltage, or alternatively, +/−10%.

The controller 1316 or 130 described in the present examples may be a digital controller or an analog controller, which generates proportional and integral terms from the difference between setpoint and average of the supply and return pressure sensors. In another embodiment of the invention, the controller is a single chip microcontroller such as an Atmel AVR processor, which provides digital signal processing capability and has built-in registers and CPU for execution of the controller process of FIG. 10 using code executed by the microprocessor. It is understood that many different types of feedback controllers are possible which operate on the setpoint and pressure sensor error voltage, including root-locus feedback controllers stabilized by use of response zeros to compensate for high frequency and low frequency poles in the response, or sigma delta controllers which perform a threshold detection on the error term. It is understood that all of these controller types known in the prior art may be used interchangably for the controller described herein.

The User Interface 152 can be any system for sending and receiving commands to the pressure controller in response to a user selection, including preferably an android tablet 661 with a built-in Bluetooth interface and antenna 663, with the command/data pairs of the UI process of FIG. 10 written using Java® code. Such a development platform provides built-in open source utilities for presentation of graphical user interfaces and deployment across many systems through a centralized update system, while preserving the security of the underlying algorithms and java code used by the user interface.

We claim:

1. A method for a pressure controller receiving a sequence of bytes from a wireless tablet, the method comprising:
    disregarding bytes received from the wireless tablet until a first byte is received with a most significant bit (MSB) of one (1), the first byte comprising bits in sequence of: 1, d7, c5, c4, c3, c2, c1, and c0, the first byte followed by a second byte with an MSB of zero (0), and comprising bits in sequence of: 0, d6, d5, d4, d3, d2, d1, and d0;
    forming an unscrambled command byte from a bit sequence comprising: 0, 0, said c5, said c4, said c3, said c2, said c1, said c0;
    when the unscrambled command byte identifies a read operation, performing a read operation on a device coupled to the pressure controller and specified by the unscrambled command byte;
    receiving a data byte from the device specified by the unscrambled command byte;
    the pressure control interface transmitting a scrambled response to the wireless tablet, the scrambled response comprising a scrambled response first byte formed by five bits of the unscrambled command byte with bit six set to an MSB value of the data byte from the device and with bit seven set to one, the scrambled response first byte followed by a scrambled response second byte, the scrambled response second byte set to the data byte from the device and with the response second byte MSB set to zero.

2. The method of claim 1 where the device is a pressure sensor.

3. The method of claim 2 where the pressure control interface and pressure sensor comprise a closed loop pressure regulation system.

4. A method for a pressure controller receiving a sequence of bytes from a wireless tablet, the method comprising:
    disregarding bytes received until a first byte is received with a most significant bit (MSB) of one (1), the first byte comprising bits in sequence of 1, d7, c5, c4, c3, c2, c1 c0, the first byte followed by a second byte with an MSB of zero (0), the second byte comprising 0, d6, d5, d4, d3, d2, d1, d0;
    forming an unscrambled command byte by re-arranging bits of the first byte and bits of the second byte into a sequence 0, 0, said said c5, said c4, said c3, said c2, said c1, said c0;
    when the unscrambled command byte identifies a write operation, performing a write operation to a device specified by the unscrambled command byte;
    receiving a data byte from the device specified by the unscrambled command byte;
    transmitting a scrambled response to the pressure control interface, the scrambled response comprising a scrambled response first byte formed by five bits of the unscrambled command byte with bit six set to an MSB value of the data byte from the device and with bit seven set to one, the scrambled response first byte followed by a zero byte.

5. The method of claim 4 where the device is a pressure regulation system.

6. The method of claim 4 where the pressure control interface is part of a closed loop pressure regulation system.

7. A method for a wireless tablet transmitting a command byte and a pressure value byte to a pressure control interface, the method comprising:
    forming a scrambled command byte from the command byte and the pressure value byte by setting the scrambled command byte MSB to one and the scrambled command byte bit to the MSB of the pressure value byte;
    forming a scrambled data byte from the pressure value byte by setting the MSB of the scrambled data byte to zero;
    transmitting the scrambled command byte and the scrambled data byte to the pressure control interface;
    upon failing to receive a first byte matching the scrambled command byte followed by a second byte matching the scrambled data byte for a read command, retransmitting the scrambled command byte followed by the scrambled data byte;
    upon failing to receive a first byte matching the scrambled command byte followed by a second byte of zero, retransmitting the scrambled command byte followed by the scrambled data byte.

8. The method of claim 7 where the remote device is a pressure regulation system.

9. The method of claim 7 where the wireless tablet includes a Bluetooth interface.

* * * * *